(12) United States Patent
Flohr et al.

(10) Patent No.: US 7,371,749 B2
(45) Date of Patent: May 13, 2008

(54) BENZOTHIAZOLE DERIVATIVES

(75) Inventors: Alexander Flohr, Reinach (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 483 days.

(21) Appl. No.: 11/183,503

(22) Filed: Jul. 18, 2005

(65) Prior Publication Data
US 2006/0019949 A1    Jan. 26, 2006

(30) Foreign Application Priority Data
Jul. 22, 2004  (EP)  ................... 04103514

(51) Int. Cl.
A61K 31/5377  (2006.01)
C07D 413/14   (2006.01)

(52) U.S. Cl. .................. 514/233.8; 544/106; 544/111; 544/133; 544/135; 514/231.2; 514/231.5; 514/233.5

(58) Field of Classification Search ............... 544/106, 544/111, 132, 133, 135; 514/231.2, 231.5, 514/233.5, 233.8
See application file for complete search history.

(56) References Cited

U.S. PATENT DOCUMENTS

| 6,599,901 B1 * | 7/2003 | Flohr et al. | 514/233.8 |
|---|---|---|---|
| 6,620,811 B2 * | 9/2003 | Flohr et al. | 514/233.8 |
| 6,727,247 B2 * | 4/2004 | Flohr et al. | 514/235.2 |
| 7,019,001 B2 * | 3/2006 | Flohr et al. | 514/233.8 |

FOREIGN PATENT DOCUMENTS

| WO | WO 01/97786    | 12/2001 |
|---|---|---|
| WO | WO 03/043634 A1 | 5/2003 |
| WO | WO 03/043636 A1 | 5/2003 |
| WO | WO 03/049741 A1 | 6/2003 |
| WO | WO 03/053946 A1 | 7/2003 |

OTHER PUBLICATIONS

Poulsen, S. A. et al., Bioorganic & Medicinal Chemistry, vol. 6 (1998) pp. 619-641.
Müller, C. E. et al., Bioorganic & Medicinal Chemistry, vol. 6 (1998), pp. 707-719.
Kim, Y. C. et al., J. Med. Chem., (1998), vol. 41, pp. 2835-2845.
Li, A. et al., J. Med. Chem., (1998), vol. 41, pp. 3186-3201.
Baraldi, P.G. et al., J. Med. Chem., (1998), vol. 41, pp. 2126-2133.
Li, A. et al., J. Med. Chem., (1999), vol. 42, pp. 706-721.
Baraldi, P. G. et al., J. Med. Chem., (1996), vol. 39, pp. 1164-1171.
Colotta, V. et al., Arch. Pharm. Med. Chem., vol. 332, pp. 39-41 (1999).
Auchampach, J. A. et al., Am. J. Physiol., vol. 276, pp. H1113-H1116 (1999).
Haas, H. L. et al., Naunyn Schmied. Arch. Pharmacol. vol. 362, pp. 375-381 (2000).
Dionisotti, S. et al., Br. J. Pharmacol. vol. 121, pp. 353-360 (1997).

* cited by examiner

Primary Examiner—Golam M. M. Shameem
(74) Attorney, Agent, or Firm—George W. Johnston; Patricia S. Rocha-Tramaloni; Kimberly J. Prior

(57) ABSTRACT

The present invention relates to compounds of formulae IA and IB

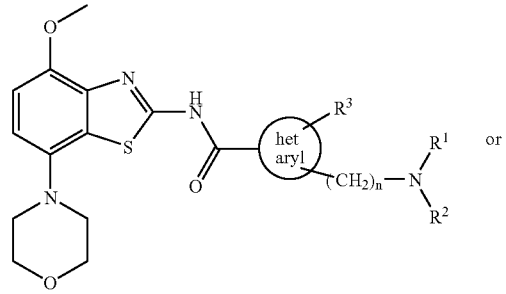

IA

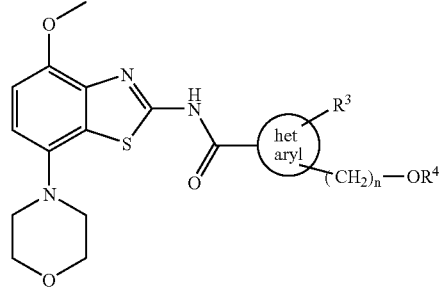

IB wherein
$R^1$ and $R^2$ are each independently lower alkyl or —($CH_2$)$_m$—O-lower alkyl, or together with the N atom to which they are attached form a heterocyclic ring;
$R^3$ is hydrogen or lower alkyl;
$R^4$ is lower alkyl;
hetaryl is 3H-imidazole-2,4-diyl or 1H-pyrazole-1,4-diyl;
n is 1 or 2; and
m is 1 or 2;

and to pharmaceutically acceptable acid addition salts thereof. These compounds may be used for the treatment of Alzheimer's disease, Parkinson's disease, Huntington's disease, neuroprotection, schizophrenia, anxiety, pain, respiration deficits, depression, ADHD, drug addiction, such as amphetamine, cocaine, opioids, ethanol, nicotine, cannabinoids, or for the treatment of asthma, allergic responses, hypoxia, ischaemia, seizure and substance abuse, or for use as sedatives, muscle relaxants, antipsychotics, antiepileptics, anticonvulsants and cardioprotective agents for coronary artery disease and heart failure.

14 Claims, No Drawings

BENZOTHIAZOLE DERIVATIVES

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A\ and\ A2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho) physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:

Bioorganic & Medicinal Chemistry, 6, (1998), 619-641,
 Bioorganic & Medicinal Chemistry, 6, (1998), 707-719,
 J. Med. Chem., (1998), 41, 2835-2845,
 J. Med. Chem., (1998), 41, 3186-3201,
 J. Med. Chem., (1998), 41, 2126-2133,
 J. Med. Chem., (1999), 42, 706-721,
 J. Med. Chem., (1996), 39, 1164-1171,
 Arch. Pharm. Med. Chem., 332, 39-41, (1999), Am. J. Physiol., 276, H1113-1116, (1999) or
Naunyn Schmied, Arch. Pharmacol. 362, 375-381, (2000).

SUMMARY OF THE INVENTION

The present invention provides compounds of the general formulae

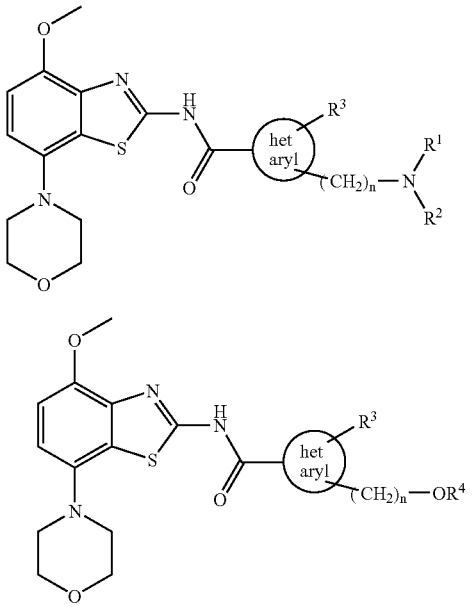

wherein
R¹ and R² are each independently lower alkyl or —(CH₂)$_m$—O-lower alkyl, or together with the N atom to which they are attached form a heterocyclic ring;
R³ is hydrogen or lower alkyl;
R⁴ is lower alkyl;
hetaryl is 3H-imidazole-2,4-diyl or 1H-pyrazole-1,4-diyl;
n is 1 or 2 and
m is 1 or 2;

and pharmaceutically acceptable acid addition salts thereof. The invention also provides methods for making such compounds.

Compounds of formulas IA or IB are adenosine receptor ligands. Specifically, the compounds of the present invention have a good affinity to the $A_{2A}$-receptor and a high selectivity to the $A_1$- and $A_3$ receptors. Thus, the present invention also provides pharmaceutical compositions which comprise a therapeutically effective amount of one or more compounds of the invention and a pharmaceutically acceptable carrier. The invention further provides methods for the treatment of diseases, related to the adenosine $A_2$ receptor, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The following definitions of general terms used in the present patent application apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "heterocyclic ring" denotes a saturated carbon ring system containing a N atom and which in addition to the N atom can contain one other heteroatom, preferably O or N-atoms. Examples of such rings are morpholin or pyrrolidin.

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

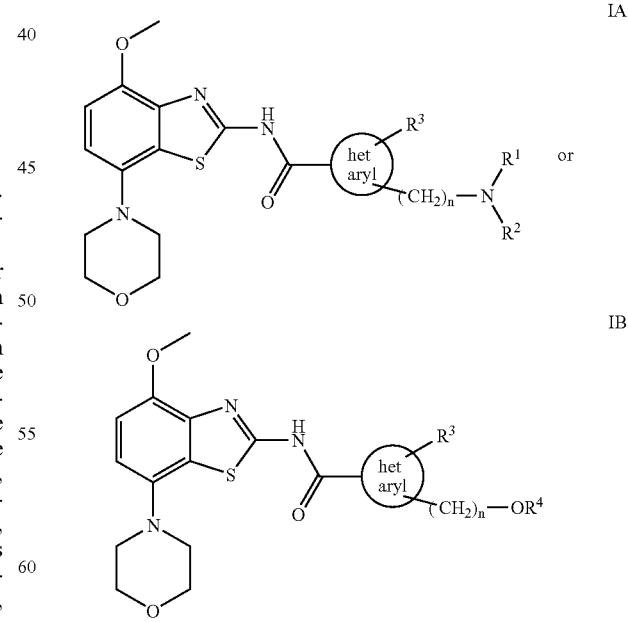

Preferred compounds of the present application are compounds of formula IA. More specifically, preferred are compounds of formula IA, wherein hetaryl is 3H-imidazole-2,4-diyl, for example the following compounds:

2-{[(2-methoxy-ethyl)-methyl-amino]-methyl}-3-methyl-3H-imidazole-4-carboxylic acid (4-methoxy-7-morpholin-4-yl-benzothiazol-2-yl)-amide,
2-dimethylaminomethyl-3-methyl-3H-imidazole-4-carboxylic acid (4-methoxy-7-morpholin-4-yl-benzothiazol-2-yl)-amide,
3-methyl-2-morpholin-4-ylmethyl-3H-imidazole-4-carboxylic acid (4-methoxy-7-morpholin-4-yl-benzothiazol-2-yl)-amide and
3-methyl-2-pyrrolidin-1-ylmethyl-3H-imidazole-4-carboxylic acid (4-methoxy-7-morpholin-4-yl-benzothiazol-2-yl)-amide.

Further preferred are compounds from formula IA wherein hetaryl is 1H-pyrazole-1,4-diyl, for example the following compounds:
1-(2-pyrrolidin-1-yl-ethyl)-1H-pyrazole-4-carboxylic acid (4-methoxy-7-morpholin-4-yl-benzo-2-yl)-amide,
1-(2-dimethylamino-ethyl)-1H-pyrazole-4-carboxylic acid (4-methoxy-7-morpholin-4-yl-benzothiazol-2-yl)-amide and
1-(2-morpholin-4-yl-ethyl)-1H-pyrazole-4-carboxylic acid (4-methoxy-7-morpholin-4-yl-benzothiazol-2-yl)-amide.

Preferred compounds of the present application are further compounds of formula IB. More specifically, preferred are compounds of formula IB, wherein hetaryl is 3H-imidazole-2,4-diyl, for example the following compound:
2-methoxymethyl-3-methyl-3H-imidazole-4-carboxylic acid (4-methoxy-7-morpholin-4-yl-benzothiazol-2-yl)-amide.

Further preferred are compounds from formula IB, wherein hetaryl is 1H-pyrazole-1,4-diyl, for example the following compound:
1-(2-methoxy-ethyl)-1H-pyrazole-4-carboxylic acid (4-methoxy-7-morpholin-4-yl-benzothiazol-2-yl)-amide.

Compounds of formulas IA and IB and their pharmaceutically acceptable salts can be prepared by methods known in the art, for example, by processes described below, which processes comprise reacting a compound of formula

II

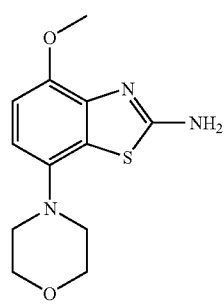

with a compound of formula

III

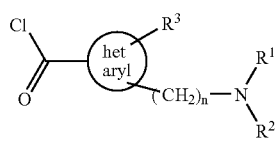

to produce a compound of formula

IA

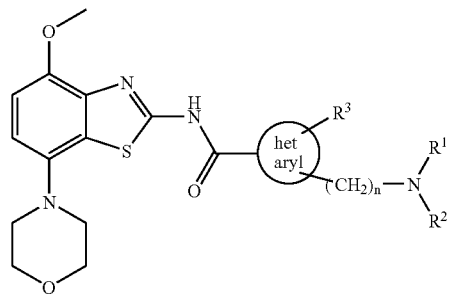

wherein $R^1$, $R^2$, $R^3$, hetaryl and n have the significances given above, or reacting a compound of formula

II

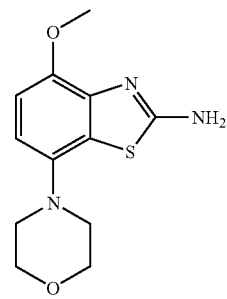

with a compound of formula

IV

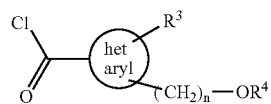

to produce a compound of formula

IB

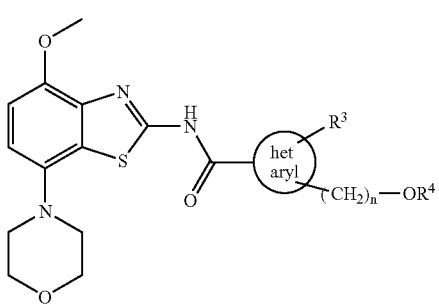

wherein $R^1$, $R^2$, $R^3$, hetaryl and n have the significances given above, and,
if desired, converting the compounds obtained into pharmaceutically acceptable acid addition salts.

In Examples 1-9 the preparation of compounds of formulas IA and IB is described in more detail.

The starting materials are known compounds or may be prepared according to methods known in the art.

Preparation of Compounds of Formulas IA and IB

The intermediate 7-(morpholin-4-yl)-4-methoxy-benzothiazol-2-ylamine can be prepared according to methods disclosed in WO01/97786. The preparation of compounds of formulas IA and IB using the intermediate of formula II is generically described in WO01/97786.

Compounds of Formula IA:

To a solution of 4-methoxy-7-morpholin-4-yl-benzothiazol-2-ylamine II in tetrahydrofurane at about −70° C. is added a solution of tert.butyllithium solution in pentane and the suspension is warmed to about −30° C. At this time, a solution of a corresponding hetaryl-carboxylic acid phenyl ester (in analogy to formula III) in tetrahydrofurane is added, and the mixture is stirred for about 1 h at room temperature. The reaction mixture is treated with saturated ammonium chloride solution, followed by ethyl acetate and the formed precipitate is collected, dried and purified in conventional manner.

Compounds of Formula IB:

The compounds of formula IB can be prepared in analogy to the above mentioned method, using 4-methoxy-7-morpholin-4-yl-benzothiazol-2-ylamine II and hetaryl-carboxylic acid phenyl ester (in analogy to formula IV).

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formulas IA or IB

The compounds of formulas IA or IB can be basic, for example in cases where the residue R contains a basic group such as an aliphatic or aromatic amine moiety. In such cases the compounds of formula I can be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formulas IA or IB can be converted to the corresponding free bases by treatment with at least a stoichiometric equivalent of a suitable base such as sodium or potassium hydroxide, potassium carbonate, sodium bicarbonate, ammonia, and the like.

The compounds of formulas IA or IB and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The pKi values of compounds of the present application are in the range of 8.8 to 9.4. The preferred compounds show a pKi>9.0.

| Example No. | $hA_2$ (pKi) |
| --- | --- |
| 1 | 9.3 |
| 2 | 9.2 |
| 3 | 9.2 |
| 4 | 8.8 |
| 5 | 9.1 |
| 6 | 9.1 |
| 7 | 9.0 |
| 8 | 9.4 |
| 9 | 9.3 |

The present invention also provides pharmaceutical compositions containing compounds of the invention, or pharmaceutically acceptable salts thereof, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions of the invention can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formulas IA or IB as well as their pharmaceutically acceptable salts are useful in the treatment or prevention of illnesses based on the adenosine receptor antagonistic activity, such as Alzheimer's disease, Parkinson's disease, Huntington's disease, neuroprotection, schizophrenia, anxiety, pain, respiration deficits, depression, ADHD, drug addiction, such as amphetamine, cocaine, opioids, ethanol, nicotine, cannabinoids, or against asthma, allergic responses, hypoxia, ischaemia, seizure and substance abuse, or are useful as sedatives, muscle relaxants, antipsychotics, antiepileptics, anticonvulsants and cardiaprotective agents for coronary artery disease and heart failure.

The most preferred indications in accordance with the present invention are those, which include disorders of the central nervous system, for example the treatment or prevention of Parkinson's disease, neuroprotection or certain depressive disorders.

Thus, the present invention provides a method for treating central nervous system disorders mediated by $A_{2A}$ which comprises administering to an individual a therapeutically effective amount of a compound of formula I. In particular, the present invention provides a method of treating Parkinson's disease which comprises administering to an individual a therapeutically effective amount of a compound of formula I. The invention also provides a method of treating depression which comprises administering to an individual a therapeutically effective amount of a compound of formula I. The invention further provides a method of neuroprotection which comprises administering to an individual a therapeutically effective amount of a compound of formula I.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injectable solutions.

The dosage at which the compounds can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | | |
|---|---|---|---|---|---|
| | | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | | mg/capsule | | |
| Item | Ingredients | 5 mg | 25 mg | 100 mg | 500 mg |
| 1. | Compound of formula I | 5 | 5 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

2-{[(2-Methoxy-ethyl)-methyl-amino]-methyl}-3-methyl-3H-imidazole-4-carboxylic acid (4-methoxy-7-morpholin-4-yl-benzothiazol-2-yl)-amide To a solution of 4-methoxy-7-morpholin-4-yl-benzothiazol-2-ylamine (220 mg, 0.83 mmol) in dry tetrahydrofurane (10 ml) at −70° C. is slowly added a solution of tert.butyl-lithium (1.1 ml of a 1.5 M solution in pentane corresponding to 1.65 mmol) and the remaining suspension slowly warmed to about −30° C. At this time, a solution of 2-{[(2-methoxy-ethyl)-methyl-amino]-methyl}-3-methyl-3H-imidazole-4-carboxylic acid phenyl ester (252 mg, 0.83 mmol) in tetrahydrofurane (4 ml) was added and the mixture stirred for 1 h at room temperature. The reaction mixture was treated with saturated aqueous ammonium chloride solution (10 ml) followed by ethyl acetate (20 ml) and the formed precipitate collected. The phases were separated and the aqueous phase extracted three times with ethyl acetate. The combined organic layers were extracted twice with water, dried with magnesium sulfate and evaporated to dryness to yield another batch of raw product. Flash-chromatography on silica (eluent trichloromethane containing 30% of ethyl acetate) yielded the title compound as white solid (31% yield). MS: m/e=475(M+H$^+$), mp 176-178° C.

Following the general method of example 1 the compounds of examples 2 to 7 were prepared.

EXAMPLE 2

2-Dimethylaminomethyl-3-methyl-3H-imidazole-4-carboxylic acid (4-methoxy-7-morpholin-4-yl-benzothiazol-2-yl)-amide Using 4-methoxy-7-morpholin-4-yl-benzothiazol-2-ylamine and 2-dimethylaminomethyl-3-methyl-3H-imidazole-4-carboxylic acid phenyl ester, the title compound was obtained as off-white solid (49% yield). MS: m/e=431(M+H$^+$), mp 229-231° C.

EXAMPLE 3

3-Methyl-2-morpholin-4-ylmethyl-3H-imidazole-4-carboxylic acid (4-methoxy-7-morpholin-4-yl-benzothiazol-2-yl)-amide Using 4-methoxy-7-morpholin-4-yl-benzothiazol-2-ylamine and 3-methyl-2-morpholin-4-ylmethyl-3H-imidazole-4-carboxylic acid phenyl ester, the title compound was obtained as off-white solid (21% yield). MS: m/e=473(M+H$^+$), mp 244-246° C.

EXAMPLE 4

3-Methyl-2-pyrrolidin-1-ylmethyl-3H-imidazole-4-carboxylic acid (4-methoxy-7-morpholin-4-yl-benzothiazol-2-yl)-amide Using 4-methoxy-7-morpholin-4-yl-benzothiazol-2-ylamine and 3-methyl-2-pyrrolidin-1-ylmethyl-3H-imidazole-4-carboxylic acid phenyl ester, the title compound was obtained as off-white solid (76% yield). MS: m/e=457(M+H$^+$), mp 255° C.

EXAMPLE 5

1-(2-Pyrrolidin-1-yl-ethyl)-1H-pyrazole-4-carboxylic acid (4-methoxy-7-morpholin-4-yl-benzothiazol-2-yl)-amide Using 4-methoxy-7-morpholin-4-yl-benzothiazol-2-ylamine and 1-(2-pyrrolidin-1-yl-ethyl)-1H-pyrazole-4-carboxylic acid ethyl ester, the title compound was obtained as white solid (13% yield). MS: m/e=457(M+H$^+$), mp 190-192° C.

EXAMPLE 6

1-(2-Dimethylamino-ethyl)-1H-pyrazole-4-carboxylic acid (4-methoxy-7-morpholin-4-yl-benzothiazol-2-yl)-amide Using 4-methoxy-7-morpholin-4-yl-benzothiazol-2-ylamine and 1-(2-dimethylamino-ethyl)-1H-pyrazole-4-carboxylic acid phenyl ester, the title compound was obtained as white crystals 54% yield). MS: m/e=431(M+H$^+$), mp 203-205° C.

EXAMPLE 7

1-(2-Morpholin-4-yl-ethyl)-1H-pyrazole-4-carboxylic acid (4-methoxy-7-morpholin-4-yl-benzothiazol-2-yl)-amide Using 4-methoxy-7-morpholin-4-yl-benzothiazol-2-ylamine and 1-(2-morpholin-4-yl-ethyl)-1H-pyrazole-4-carboxylic acid phenyl ester, the title compound was obtained as white crystals 42% yield). MS: m/e=473(M+H$^+$), mp 204-207° C.

EXAMPLE 8

1-(2-Methoxy-ethyl)-1H-pyrazole-4-carboxylic acid (4-methoxy-7-morpholin-4-yl-benzothiazol-2-yl)-amide Using 4-methoxy-7-morpholin-4-yl-benzothiazol-2-ylamine and 1-(2-methoxy-ethyl)-1H-pyrazole-4-carboxylic acid phenyl ester, the title compound was obtained as light yellow crystals 43% yield). MS: m/e=418(M+H$^+$), mp 191-193° C.

EXAMPLE 9

2-Methoxymethyl-3-methyl-3H-imidazole-4-carboxylic acid (4-methoxy-7-morpholin-4-yl-benzothiazol-2-yl)-amide Using 4-methoxy-7-morpholin-4-yl-benzothiazol-2-ylamine and 2-methoxymethyl-3-methyl-3H-imidazole-4-carboxylic acid phenyl ester, the title compound was obtained as white crystals 48% yield). MS: m/e=418(M+H$^+$), mp 242-245° C.

Intermediates

EXAMPLE 10

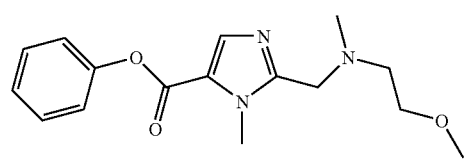

2-{[(2-Methoxy-ethyl)-methyl-amino]-methyl}-3-methyl-3H-imidazole-4-carboxylic acid phenyl ester To a solution of 1-{2-[(2-methoxy-ethyl)-methyl-amino]-ethyl}-1H-pyrazole-4-carboxylic acid (467 mg, 1.54 mmol) and phenol (145 mg, 1.54 mmol) in dimethylformamide (8 ml) was added under argon at 0° C. a solution of 4-dimethylaminopyridine (94 mg, 0.77 mmol) and brom-tripyrrolidinophosphonium-hexafluorophosphat (790 mg, 0.70 mmol) in dimethylformamide (8 ml) followed by triethylamine (0.65 ml, 4.6 mmol). After 48 h at ambient temperature, the reaction mixture is treated with saturated aqueous ammonium chloride (25 ml) and extracted three times with ethyl acetate (25 ml each). The combined organic layers are dryed with magnesium sulphate and evaporated to dryness. Flash chromatography (silice, eluent dichloromethane containing 4% methanol) afforded the title compound as colorless oil (55% yield). MS: m/e=304(M+H$^+$).

Following the general method of example 10 the compounds of examples 11 to 16 were prepared.

EXAMPLE 11

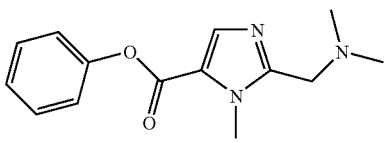

2-Dimethylaminomethyl-3-methyl-3H-imidazole-4-carboxylic acid phenyl ester

Using 2-dimethylaminomethyl-3-methyl-3H-imidazole-4-carboxylic acid, the title compound was obtained as light brown wax (43% yield). MS: m/e=260(M+H$^+$).

EXAMPLE 12

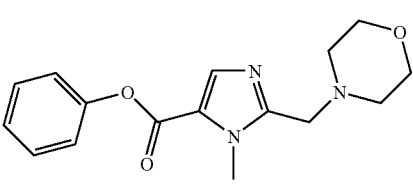

3-Methyl-2-morpholin-4-ylmethyl-3H-imidazole-4-carboxylic acid phenyl ester

Using 3-methyl-2-morpholin-4-ylmethyl-3H-imidazole-4-carboxylic acid, the title compound was obtained as colorless wax (40% yield). MS: m/e=302(M+H$^+$).

EXAMPLE 13

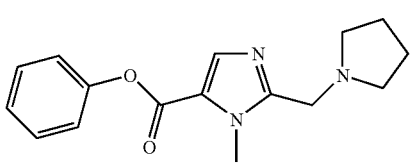

3-Methyl-2-pyrrolidin-1-ylmethyl-3H-imidazole-4-carboxylic acid phenyl ester

Using 3-methyl-2-pyrrolidin-1-ylmethyl-3H-imidazole-4-carboxylic acid, the title compound was obtained as brown oil (22% yield). MS: m/e=286(M+H$^+$).

EXAMPLE 14

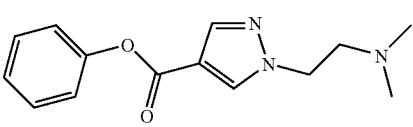

1-(2-Dimethylamino-ethyl)-1H-pyrazole-4-carboxylic acid phenyl ester

Using 1-(2-dimethylamino-ethyl)-1H-pyrazole-4-carboxylic acid, the title compound was obtained as colorless liquid (56% yield). MS: m/e=260(M+H$^+$).

EXAMPLE 15

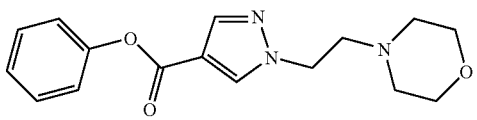

1-(2-Morpholin-4-yl-ethyl)-1H-pyrazole-4-carboxylic acid phenyl ester

Using 1-(2-morpholin-4-yl-ethyl)-1H-pyrazole-4-carboxylic acid, the title compound was obtained as white solid (33% yield). MS: m/e=302(M+H$^+$), mp 73-76° C.

EXAMPLE 16

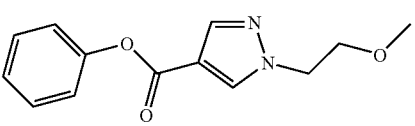

1-(2-Methoxy-ethyl)-1H-pyrazole-4-carboxylic acid phenyl ester

Using, 1-(2-methoxy-ethyl)-1H-pyrazole-4-carboxylic acid, the title compound was obtained as colorless oil (55% yield). MS: m/e=247(M−H$^+$).

EXAMPLE 17

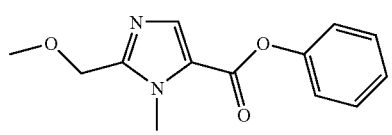

2-Methoxymethyl-3-methyl-3H-imidazole-4-carboxylic acid phenyl ester

Using, 2-methoxymethyl-3-methyl-3H-imidazole-4-carboxylic acid, the title compound was obtained as light yellow solid (39% yield). MS: m/e=247(M−H$^+$), mp 54-58° C.

EXAMPLE 18

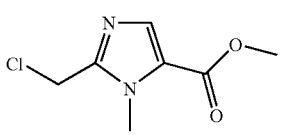

2-Chloromethyl-3-methyl-3H-imidazole-4-carboxylic acid methyl ester hydrochloride A solution of 2-hydroxymethyl-3-methyl-3H-imidazole-4-carboxylic acid methyl ester (250 mg, 1.5 mmol) in ethyl acetate/methanol 6 ml, 1:1) was converted to the hydrochloride by usage of an excess of an etheral solution of hydrogen chloride. After evaporation, the light brown residue was treated with thionyl chloride (1.1 ml, 15 mmol) and stirred

EXAMPLE 19

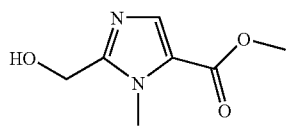

2-Hydroxymethyl-3-methyl-3H-imidazole-4-carboxylic acid methyl ester

A suspension of 3-methyl-3H-imidazole-4-carboxylic acid methyl ester (4.0 g, 29 mmol) and paraformaldehyde (18 g, corresponding to 570 mmol) in methanol (40 ml) was heated in a sealed vessel to 135° C. for 60 h. After cooling to ambient temperature, the solution was evaporated to dryness. Flash chromatography (silica, eluent dichloromethane containing 5% methanol) afforded the title compound as white crystals (56% yield). MS: m/e=171(M+H$^+$), mp 145-147° C.

EXAMPLE 20

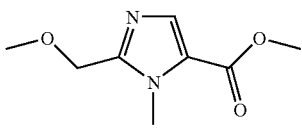

2-Methoxymethyl-3-methyl-3H-imidazole-4-carboxylic acid methyl ester

A solution of 2-hydroxymethyl-3-methyl-3H-imidazole-4-carboxylic acid methyl ester (250 mg, 1.5 mmol) in dimethylformamide (10 ml) is subsequently treated with sodium hydride (71 mg 60% dispersion in mineral oil, 1.8 mmol) and after 0.5 h with dimethyl sulfate (0.17 ml, 1.8 mmol). After 1 h at ambient temperature, the volatile componantes are removed in vacuo, the residue taken up in ethyl acetate (20 ml) and water (20 ml) and the phases separated. The aqueous phase is extracted twice with ethyl acetate (20 ml each) and the combined organic layers are dried with magnesium sulfate and evaporated to dryness. Flash chromatography (silica, eluent dichloromethane containing 4% methanol) afforded the title compound as white crystals (42% yield). MS: m/e=185(M+H$^+$), mp 74-77° C.

EXAMPLE 21

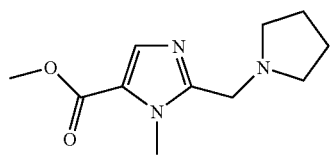

3-Methyl-2-pyrrolidin-1-ylmethyl-3H-imidazole-4-carboxylic acid methyl ester

2-Chloromethyl-3-methyl-3H-imidazole-4-carboxylic acid methyl ester hydrochloride (224 mg, 1 mmol) was dissolved in pyrrolidine (2.3 ml, 28 mmol) and stirred at ambient temperature for, the title compound was obtained as light yellow oil 45 min. After evaporation to dryness, the residue is taken up in ethyl acetate and saturated aqueous sodium carbonate (20 ml) and the phases separated. The aqueous phase is extracted twice with ethyl acetate (20 ml each) and the combined organic layers are dried with magnesium sulfate and evaporated to dryness. Flash chromatography (silica, eluent dichloromethane7methanol 19:1) afforded the title compound as light yellow oil (61% yield). MS: m/e=224(M+H$^+$).

Following the general method of example 21 the compounds of examples 22 to 24 were prepared.

EXAMPLE 22

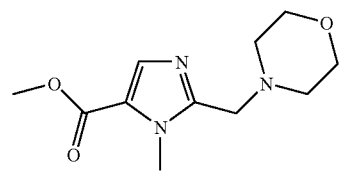

3-Methyl-2-morpholin-4-ylmethyl-3H-imidazole-4-carboxylic acid methyl ester

Using 2-chloromethyl-3-methyl-3H-imidazole-4-carboxylic acid methyl ester hydrochloride and morpholine, the title compound was obtained as light brown solid (>98% yield). MS: m/e=240(M+H$^+$).

EXAMPLE 23

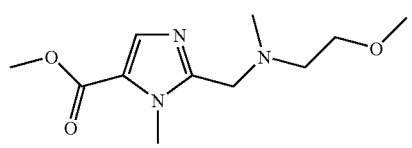

2-{[(2-Methoxy-ethyl)-methyl-amino]-methyl}-3-methyl-3H-imidazole-4-carboxylic acid methyl ester Using 2-chloromethyl-3-methyl-3H-imidazole-4-carboxylic acid methyl ester hydrochloride and (2-methoxyethyl)-methyl-amine, the title compound was obtained as light brown viscous oil (92% yield). MS: m/e=242(M+H$^+$).

EXAMPLE 24

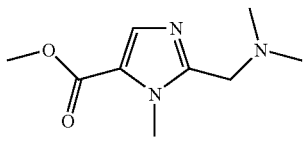

2-Dimethylaminomethyl-3-methyl-3H-imidazole-4-carboxylic acid methyl ester

Using 2-chloromethyl-3-methyl-3H-imidazole-4-carboxylic acid methyl ester hydrochloride and dimethylamine (33% solution in ethanol), the title compound was obtained as brown viscous oil (85% yield). MS: m/e=198(M+H$^+$).

EXAMPLE 25

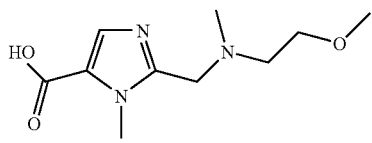

2-{[(2-Methoxy-ethyl)-methyl-amino]-methyl}-3-methyl-3H-imidazole-4-carboxylic acid 2-{[(2-Methoxy-ethyl)-methyl-amino]-methyl}-3-methyl-3H-imidazole-4-carboxylic acid methyl ester (380 mg, 1.58 mmol) were dissolved in methanol (4.5 ml) and treated with water (0.39 ml) and lithium hydroxide monohydrate (80 mg, 1.89 mmol) and stirred for 18 h at ambient temperature. The reaction mixture is the carefully acidified at 0° C. with 1N hydrochloric acid and evaporated to dryness. The title compound was obtained as mixture with lithium chloride and used without further purification. Light brown solid (>98% yield by 1H-NMR). MS: m/e=226(M−H$^+$).

Following the general method of example 25 the compounds of examples 26 to 28 were prepared.

EXAMPLE 26

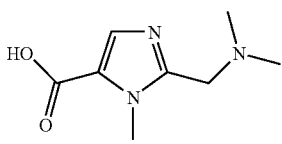

2-Dimethylaminomethyl-3-methyl-3H-imidazole-4-carboxylic acid

Using 2-dimethylaminomethyl-3-methyl-3H-imidazole-4-carboxylic acid methyl ester, the title compound was obtained as light brown solid (>98% yield by 1H-NMR). MS: m/e=182(M−H$^+$).

EXAMPLE 27

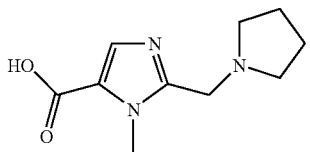

3-Methyl-2-pyrrolidin-1-ylmethyl-3H-imidazole-4-carboxylic acid

Using 3-methyl-2-pyrrolidin-1-ylmethyl-3H-imidazole-4-carboxylic acid methyl ester, the title compound was obtained as brown wax (>98% yield by 1H-NMR). MS: m/e=208(M−H$^+$).

EXAMPLE 28

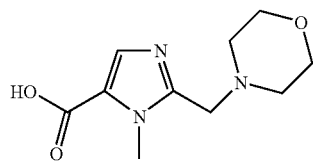

3-Methyl-2-morpholin-4-ylmethyl-3H-imidazole-4-carboxylic acid

Using 3-methyl-2-morpholin-4-ylmethyl-3H-imidazole-4-carboxylic acid methyl ester, the title compound was obtained as light brown solid (>98% yield by 1H-NMR). MS: m/e=224(M−H$^+$).

EXAMPLE 29

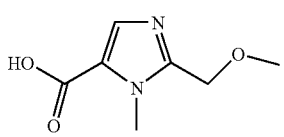

2-Methoxymethyl-3-methyl-3H-imidazole-4-carboxylic acid

Using 2-methoxymethyl-3-methyl-3H-imidazole-4-carboxylic acid methyl ester, the title compound was obtained as brown solid and used without further characterization.

EXAMPLE 30

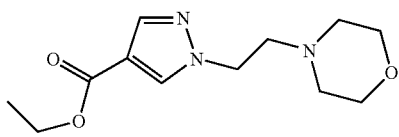

1-(2-Morpholin-4-yl-ethyl)-1H-pyrazole-4-carboxylic acid ethyl ester

1H-Pyrazole-4-carboxylic acid (300 mg, 2.1 mmol), 4-(2-chloroethyl)morpholine (822 mg, 4.3 mmol) and potassium carbonate (1.2 g, 8.6 mmol) are dissolved in dimethylformamide (12 ml) and stirred for 6.5 h at 75° C. After standing for another 18 h at ambient temperature, the reaction mixture was treated with water (25 ml) and extracted four times with ethyl acetate (25 ml each). The combined organic layers are extracted four times with water, dryed with magnesium sulphate and evaporated in vacuo. Flash chromatography (silice, eluent dichloromethane containing 4% methanol) afforded the title compound as colorless liquid (70% yield). MS: m/e=254(M+H$^+$).

Following the general method of example 30 the compounds of examples 31 to 32 were prepared.

EXAMPLE 31

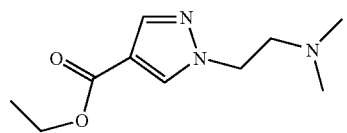

1-(2-Dimethylamino-ethyl)-1H-pyrazole-4-carboxylic acid ethyl ester

Using 1H-pyrazole-4-carboxylic acid and (2-chloro-ethyl)-dimethyl-amine, the title compound was obtained as colorless liquid (72% yield). MS: m/e=212(M+H$^+$).

EXAMPLE 32

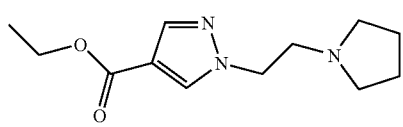

1-(2-Pyrrolidin-1-yl-ethyl)-1H-pyrazole-4-carboxylic acid ethyl ester

Using 1H-pyrazole-4-carboxylic acid and 1-(2-chloro-ethyl)-pyrrolidine, the title compound was obtained as light brown oil (65% yield). MS: m/e=238(M+H$^+$).

EXAMPLE 33

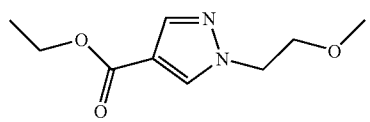

1-(2-Methoxy-ethyl)-1H-pyrazole-4-carboxylic acid ethyl ester

Using 1H-pyrazole-4-carboxylic acid and 2-bromoethyl methyl ether, the title compound was obtained as colorless oil (67% yield). MS: m/e=199(M+H$^+$).

EXAMPLE 34

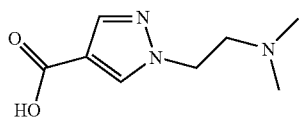

1-(2-Dimethylamino-ethyl)-1H-pyrazole-4-carboxylic acid

Using 1-(2-dimethylamino-ethyl)-1H-pyrazole-4-carboxylic acid ethyl ester, the title compound was prepared in the same manner as described for 2-{[(2-methoxy-ethyl)-methyl-amino]-methyl}-3-methyl-3H-imidazole-4-carboxylic acid. White solid (>98% yield by $^1$H-NMR). MS: m/e=184(M+H$^+$).

EXAMPLE 35

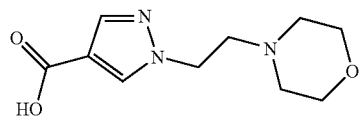

Using 1-(2-morpholin-4-yl-ethyl)-1H-pyrazole-4-carboxylic acid ethyl ester, the title compound was obtained as light yellow solid and used without further characterization. MS: m/e=224(M−H$^+$).

EXAMPLE 36

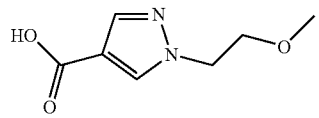

1-(2-Methoxy-ethyl)-1H-pyrazole-4-carboxylic acid

Using, 1-(2-methoxy-ethyl)-1H-pyrazole-4-carboxylic acid ethyl ester, the title compound was obtained as colorless oil and used without further characterization. MS: m/e=169 (M−H$^+$).

The invention claimed is:

1. A compound of formulae IA or IB

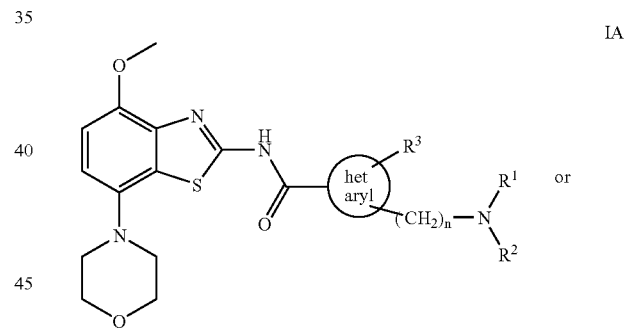

wherein

R$^1$ and R$^2$ are each independently lower alkyl or —(CH$_2$)$_m$—O-lower alkyl, or together with the N atom to which they are attached form a heterocyclic ring;

$R^3$ is hydrogen or lower alkyl;

$R^4$ is lower alkyl;

hetaryl is 3H-imidazole-2,4-diyl or 1H-pyrazole-1,4-diyl;

n is 1 or 2 and m is 1 or 2;

or a pharmaceutically acceptable acid addition salt thereof.

2. A compound of formula IA according to claim 1.

3. A compound according to claim 2, wherein the hetaryl group is 3H-imidazole-2,4-diyl.

4. A compound according to claim 3, selected from the group consisting of

2-{[(2-methoxy-ethyl)-methyl-amino]-methyl}-3-methyl-3H-imidazole-4-carboxylic acid (4-methoxy-7-morpholin-4-yl-benzothiazol-2-yl)-amide, 2-dimethylaminomethyl-3-methyl-3H-imidazole-4-carboxylic acid (4-methoxy-7-morpholin-4-yl-benzothiazol-2-yl)-amide, 3-methyl-2-morpholin-4-ylmethyl-3H-imidazole-4-carboxylic acid (4-methoxy-7-morpholin-4-yl-benzothiazol-2-yl)-amide and 3-methyl-2-pyrrolidin-1-ylmethyl-3H-imidazole-4-carboxylic acid (4-methoxy-7-morpholin-4-yl-benzothiazol-2-yl)-amide.

5. A compound according to claim 2, wherein the hetaryl group is 1H-pyrazole-1,4-diyl.

6. A compound according to claim 5, selected from the group consisting of 1-(2-pyrrolidin-1-yl-ethyl)-1H-pyrazole-4-carboxylic acid (4-methoxy-7-morpholin-4-yl-benzothiazol-2-yl)-amide, 1-(2-dimethylamino-ethyl)-1H-pyrazole-4-carboxylic acid (4-methoxy-7-morpholin-4-yl-benzothiazol-2-yl)-amide and 1-(2-morpholin-4-yl-ethyl)-1H-pyrazole-4-carboxylic acid (4-methoxy-7-morpholin-4-yl-benzothiazol-2-yl)-amide.

7. A compound of formula IB according to claim 1.

8. A compound according to claim 7, wherein the hetaryl group is 3H-imidazole-2,4-diyl.

9. A compound according to claim 8, wherein the compound is 2-methoxymethyl-3-methyl-3H-imidazole-4-carboxylic acid (4-methoxy-7-morpholin-4-yl-benzothiazol-2-yl)-amide.

10. A compound according to claim 7, wherein the hetaryl group is 1H-pyrazole-1,4-diyl.

11. A compound according to claim 10, wherein the compound is 1-(2-methoxy-ethyl)-1H-pyrazole-4-carboxylic acid (4-methoxy-7-morpholin-4-yl-benzothiazol-2-yl)-amide.

12. A pharmaceutical composition comprising a therapeutically effective amount of a compound of formula IA or IB

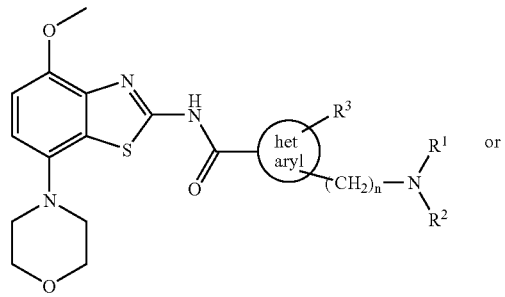

IA

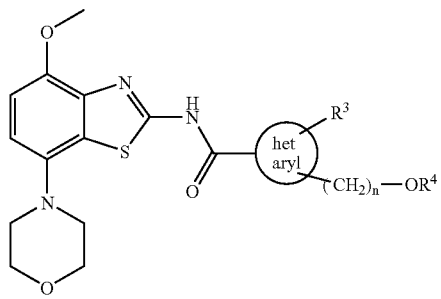

IB wherein $R^1$ and $R^2$ are each independently lower alkyl or —$(CH_2)_m$—O-lower alkyl, or together with the N atom to which they are attached form a heterocyclic ring;

$R^3$ is hydrogen or lower alkyl;

$R^4$ is lower alkyl;

hetaryl is 3H-imidazole-2,4-diyl or 1H-pyrazole-1,4-diyl;

n is 1 or 2 and m is 1 or 2;

or a pharmaceutically acceptable acid addition salt thereof and a pharmaceutically acceptable carrier.

13. A process for preparing a compound of formula IA,

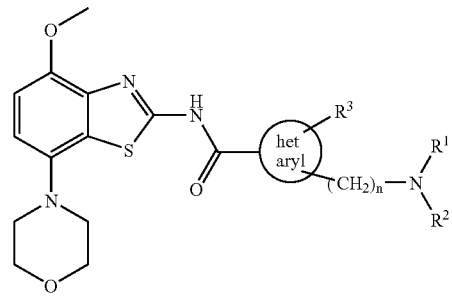

IA wherein $R^1$ and $R^2$ are each independently lower alkyl or —$(CH_2)_m$—O-lower alkyl, or together with the N atom to which they are attached form a heterocyclic ring;

R³ is hydrogen or lower alkyl;
hetaryl is 3H-imidazole-2,4-diyl or 1H-pyrazole-1,4-diyl;
n is 1 or 2 and
m is 1 or 2;
which process comprises
  a) reacting a compound of formula

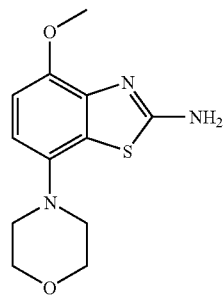

II with a compound of formula

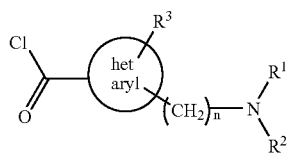

III to produce a compound of formula

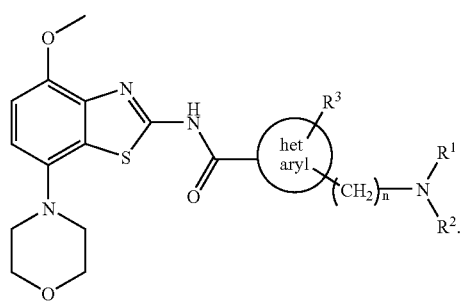

IA

14. A process for preparing a compound of formula IB,

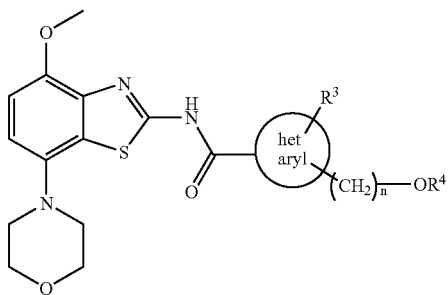

IB wherein
  R¹ and R² are each independently lower alkyl or
    —(CH₂)$_m$—O-lower alkyl, or together with the N
    atom to which they are attached form a heterocyclic
    ring;
  R⁴ is lower alkyl;
  hetaryl is 3H-imidazole-2,4-diyl or 1H-pyrazole-1,4-diyl;
  n is 1 or 2 and
  m is 1 or 2;
which process comprises
  a) reacting a compound of formula

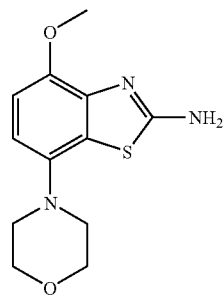

II with a compound of formula

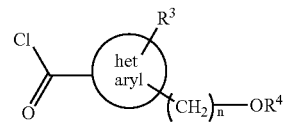

IV to a compound of formula

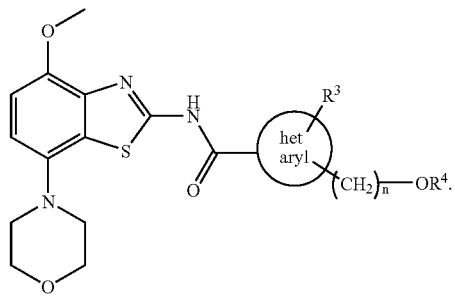

IB

* * * * *